(12) United States Patent
Reynolds (10) Patent No.: US 6,189,560 B1
(45) Date of Patent: Feb. 20, 2001

(54) CONNECTOR ASSEMBLY FOR MEDICAL GAS SERVICE OUTLET

(75) Inventor: Kenneth Joseph Reynolds, Caledon (CA)

(73) Assignee: VitalAire, Mississauga (CA)

( * ) Notice: Under 35 U.S.C. 154(b), the term of this patent shall be extended for 0 days.

(21) Appl. No.: 09/484,430

(22) Filed: Jan. 18, 2000

(51) Int. Cl.$^7$ ....................................................... F16L 5/00
(52) U.S. Cl. .................... 137/360; 137/329.1; 137/329.4
(58) Field of Search ............................. 137/329.1, 329.2, 137/329.4, 360

(56) References Cited

U.S. PATENT DOCUMENTS

| | | | | |
|---|---|---|---|---|
| 2,905,487 | * | 9/1959 | Shifter | 137/329.1 |
| 3,170,667 | * | 2/1965 | Szohatzky | 137/360 |
| 3,477,105 | * | 11/1969 | Cranage | 137/360 |
| 4,344,455 | * | 8/1982 | Norton et al. | 137/329.4 |
| 4,683,905 | * | 8/1987 | Vigneau et al. | 137/329.1 |
| 5,197,511 | * | 3/1993 | Kohn et al. | 137/360 |

* cited by examiner

Primary Examiner—A. Michael Chambers
(74) Attorney, Agent, or Firm—Diller, Ramik & Wight, PC (57) ABSTRACT

A secondary valve unit is provided to interconnect a front/finish assembly and an existing wall outlet for supplying medical gases. The secondary valve unit includes a cylindrical body containing a secondary valve assembly to prevent gas leakage when the front unit that contains a primary valve is removed for services. The secondary valve unit is pre-assembled and threadedly connected to the wall outlet. The threaded connection is locked by an indexing plate which is attached to the wall and provides indexing connection with the front unit to avoid mistakenly connecting a wrong front unit for different gases. The secondary valve unit is especially used in renovations of medical gas systems in hospitals, and able to be installed to an existing wall outlet without breaking the wall so that the cost for renovations is significantly reduced. The connector assembly for gases using the secondary valve unit provides a great gas flow and achieves a more secure connection over a long period of time.

20 Claims, 8 Drawing Sheets

CONNECTOR ASSEMBLY FOR MEDICAL GAS SERVICE OUTLET

TECHNICAL FIELD

This invention relates to medical gas service outlets and, more particularly, to an adaptor kit for medical gases used to connect an existing wall outlet back body of a medical gas piping system to a front/finish assembly having a valve tube type of interface.

BACKGROUND OF THE INVENTION

It is normal in most hospitals today to provide in-room service of a various medical gases such as oxygen, air, nitrous oxide, as well as a source of vacuum for suction equipment. The gases are generally provided under pressure or vacuum from a central source. A user can conveniently plug in the various equipment that utilize the particular service with a specially designed, keyed adapter that is generally connected to medical tubing for delivery to its end use device.

A typical connector assembly for medical gases usually includes a wall outlet having a cylindrical housing in fluid communication with a specified gas source and being fixed in the wall during construction, and a front unit which is a gas specific portion for gases such as oxygen, nitrous oxide and air, defining diameter-indexed two-stage bores.

A primary valve is provided within a tubing of the front unit which is usually in a closed position and can be pressed-open by a plunger of the adapter at the ends of hoses or gas-using devices.

A secondary valve is provided within the cylindrical body installed in the wall, which is pressed in an open position by the tubing of the front unit when the front unit is connected to the wall outlet. The secondary valve returns to a closed position to prevent gas leakage through the wall outlet when the front unit is removed from the wall outlet for services, such as cleaning or repair.

Typical examples of the connector assemblies for medical gases are described in U.S. Pat. No. 3,563,267 which issued to Thompson on Feb. 16, 1971, U.S. Pat. No. 4,190,075, which issued to Kayser on Feb. 26, 1980 and U.S. Pat. No. 5,236,005, which issued to Berg on Aug. 17, 1993.

As technology develops, the connector assemblies for medical gases are improved. New connector assemblies with updated technologies can be conveniently installed during construction of buildings. However, it is not convenient to install new connector assemblies for replacing old ones in renovations of the medical gas systems in hospitals. A wall outlet containing the secondary valve is usually welded to a gas supply pipe, both being buried within the wall. The decorative exterior of the wall, surrounding the wall outlet, has to be demolished and the existing wall outlet has to be cut from the pipe in order to substitute a new connector assembly. After the wall outlet of the new connector assembly is welded to the pipe in the wall, the wall must be mended with new cladding material. It is a costly process.

Therefore, a structure of connector assemblies for medical gases is desirable to enable the connector assemblies to be detachably connected with existing wall outlets in order to avoid the demolition process during renovations of medical gas systems.

Improved connector assemblies for gases which can be conveniently connected to an existing wall outlet of one type is described, for example, in U.S. Pat. No. 4,562,856, which issued to Garvey et al., on Jan. 7, 1986. A major aspect of the device described in this U.S. Patent, is to incorporate the primary valve and the secondary valve into a single cylindrical body which has a threaded front end conforming to D.I.S.S. (Diameter Indexing Safety System) standard and a threaded rear end for threadedly engaging a corresponding threaded connector defined in an existing wall outlet. This ensures that the internal indexing diameters are not removed during servicing because the cylindrical body is to be left affixed to its primary attachment.

The single body structure, however, leads to problems regarding safety issues. A liquid thread locker, Loctite 271, is applied on the threaded rear end of the cylindrical body to lock the threaded connection with the wall outlet after the liquid becomes solid. The thread locker is an inflammable material, especially in an oxygen-rich environment. The high operating pressure, at 50 psi required in an oxygen system in hospitals increases the risks of igniting the material. It is apparent that the device is not suitable for use relating to an oxygen supply system. After a long period of time, the solid material ages and loses its locking function. Frequent engaging and disengaging adapters to and from the threaded front end of the cylindrical body may eventually loosen the threaded connection between the rear end of the cylindrical body and the wall outlet. Therefore, there is a risk of suddenly losing the connection, and the device under the pressure of 50 psi may eject from the wall outlet.

A structure of a connector assembly for medical gases with improvements regarding a large gas flow is also desirable. A pressure drop through the connector assembly is expected not more than 4 psi according to the standard. Most devices in prior art have a pressure drop of about 8 to 12 psi and the device suggested in U.S. Pat. No. 4,562,856 has a pressure drop ranged from 6 to 8 psi.

SUMMARY OF THE INVENTION

It is one object of the present invention to provide a connector assembly for medical gases, which overcomes the shortcomings in the prior art.

It is another object of the invention to provide a connector assembly for medical gases, which improves the gas flow.

It is a further object of the invention to provide a connector assembly for medical gases, which is an improvement in respect to safety issues.

It is yet a further object of the invention to provide an adapter kit for a connector unit for gases which is used to connect a front unit having a primary valve in a tubing to an existing wall outlet in fluid communication with a medical gas source, so to eliminate the need for extensive renovations of medical gas systems and reduce the cost thereof.

It is yet a further object of the invention to provide a pre-assembled connector unit including a secondary valve to be installed to an existing wall outlet in fluid communication with a medical gas source and adapted to receive a front unit having a primary valve so to eliminate the need for extensive renovations of medical gas systems and reduce the cost thereof.

In general terms, a cylindrical body is provided to contain all inner parts of the secondary valve therein and adapted to be conveniently and detachably connected to an existing wall outlet of a gas system for detachably receiving a front unit.

More specifically, according to one aspect of the invention, a kit is provided for a connector unit for gases which is used to connect a wall outlet of a gas system to a front unit having a primary valve tube, the kit comprising:

a cylindrical body adapted to be detachably connected with the wall outlet, and defining an axial passage extending therethrough; a secondary valve adapted to be secured to by the cylindrical body, the secondary valve being biased to close the axial passage when the cylindrical body is connected to the wall outlet and being always open when the front unit is mounted to the wall and the primary valve tube is inserted into the passage of the body; a seal adapted to be contained within the cylindrical body for sealing an exterior of the primary valve tube when the front unit is mounted to the wall; and means for securing the connector unit to the wall outlet when the cylindrical body is connected to the wall outlet.

The kit preferably includes a plate, having an aperture, adapted to be attached to a front end of the cylindrical body, with the aperture aligned with the passage of the cylindrical body, for securing the connector unit to the wall while permitting the tubing of the front unit to be inserted through the aperture into the passage of the cylindrical body; and indexing means provided with the plate, adapted for co-operation with corresponding indexing means of the front unit to ensure that a front unit only specified for use with a gas of the type supplied from the wall outlet is enabled to be connected to the connector unit.

The connector unit assembled using the kit is preferably threadedly connected at a rear end of the cylindrical body to the wall outlet, and a holding bracket and resilient gasket firmly secure the cylindrical body to the plate to prevent the cylindrical body from rotation relative to the plate which is attached to the wall. Therefore, the threaded connection of the cylindrical body with the wall outlet is safely locked.

The connector unit for gases according to the invention advantageously facilitate renovations of existing medical gas systems in hospitals. A kit may include parts for different connector units which can be conveniently installed to different vintages and manufacturers of medical gas wall outlets without the wall demolition process, and all the adaptor kits accept the AMICO front/finish assembly specified for different types of medical gases. Thus, the estimated average cost for upgrading the existing wall outlet assembly, according to the present invention, is significantly reduced.

The risk of losing connection is eliminated because not only the cylindrical body is prevented from rotation by the attachment to the plate but also the engaging or disengaging action on the front unit has little effect in respect to the threaded connection between the upgrade kit and the wall outlet. The upgrade kit according to the invention is able to provide a large gas flow and the total pressure drop is reduced to a range from 1.9 to 2.0 psi.

Other features and advantages of the invention will be apparent from the description of the preferred embodiments.

BRIEF DESCRIPTION OF THE DRAWINGS

Having thus generally described the nature of the invention, reference will now be made to the preferred embodiments thereof and the accompanying drawings, in which:

FIG. 8b is a perspective view of an interchangeable tool tip for the tool shown in FIG. 8a; and FIG. 8c appears on the sheet of FIG. 1b and is a rear view of the tool in FIG. 8a.

DETAILED DESCRIPTION OF THE PREFERRED EMBODIMENT

Figure 1A:
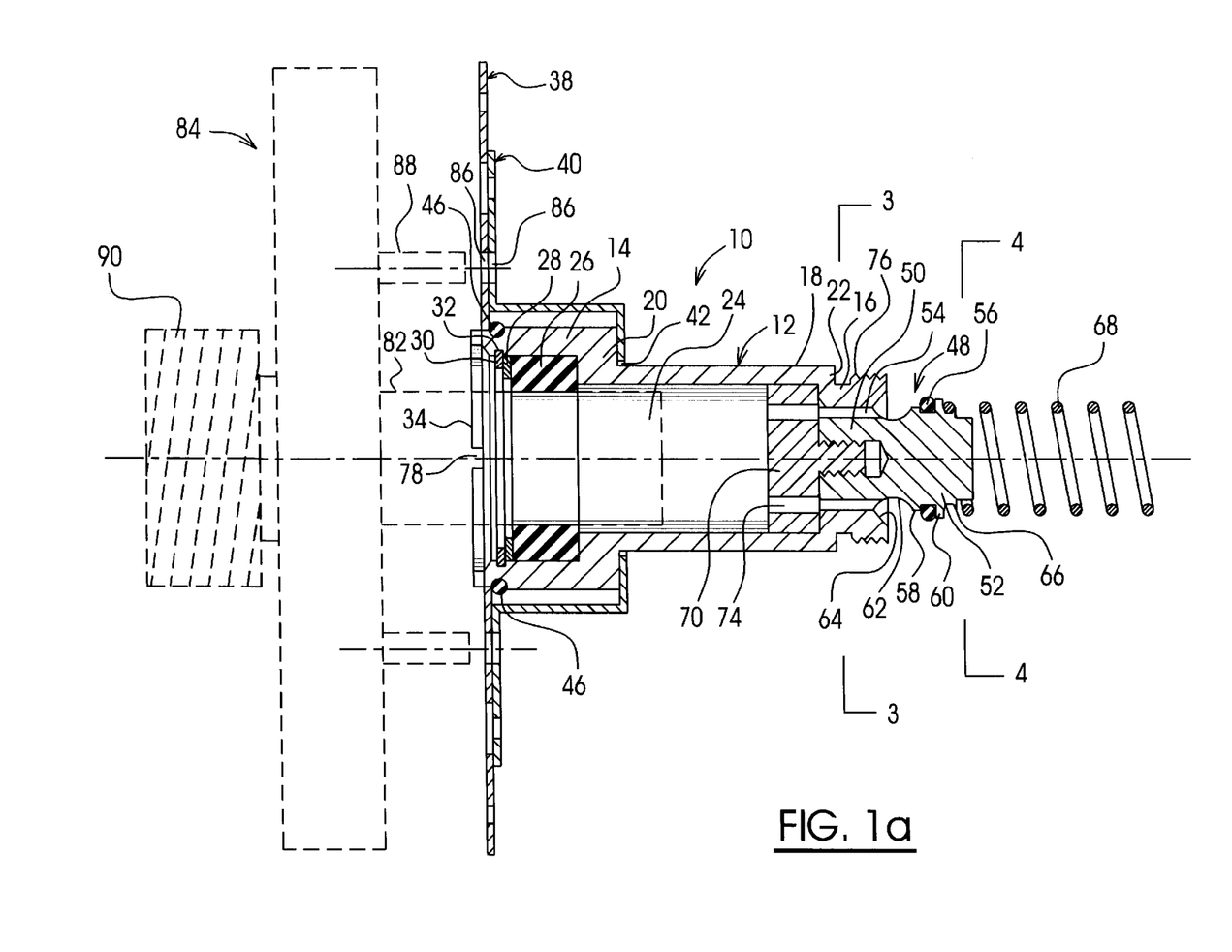
FIG. 1a is a longitudinal cross-sectional view of the preferred embodiment of the invention, in which a secondary valve is in an open position.

Referring now to the drawings, there is shown in FIG. 1a, a pre-assembled secondary valve unit 10 which includes a cylindrical body 12 having a front portion 14, a rear portion 16 and a middle portion 18. Each of the portions 14, 16 and 18 has an external diameter and an internal diameter and those external and internal diameters decrease in a sequence from the front portion 14 to the rear portion 16 as to form a front radial section 20 and a rear radial section 22 as well as an axial passage 24 extending through the cylindrical body 12.

An annular resilient seal 26 is provided within the front portion 14 abutting, at its rear side, against the inner surface of the front radial section 20 and is covered by a washer 28 at its front side. The washer 28 is in turn axially restrained by an annular spring retainer 30 which is received in an annular groove 32 inside the front portion 14 at the front end. An annular ridge 34 has an external diameter slightly smaller than the outer diameter of the front portion 14 and protrudes axially from the front end of the cylindrical body 12, fitting into an aperture 36 (see FIG. 2) of an indexing plate 38 which is attached to the cylindrical body 12 using a recessed bracket 40.

The bracket 40 has a central aperture 42 for receiving the middle portion 18 of the cylindrical body 12 extending therethrough, and bent in a shape, as shown in FIG. 1a to abut the external surface of the front radial section 20. The bracket 40 is fastened to the indexing plate 38 using screws (not shown) through the bores 44 defined in the indexing plate 38 and the bracket 40, respectively. The bores 44 defined in the bracket are threaded and, therefore, no nuts are needed to threadedly fasten the screw in the bores 44.

A gasket 46 is received in an annular groove provided on the exterior of the annular ridge 34 adjacent the front end of the front portion 14 of the cylindrical body 12. The gasket 46 is compressed between the indexing plate 38 and the front end of the cylindrical body 12 to ensure a firm and secure attachment so as to prevent the cylindrical body 12 from rotation relative to the indexing plate 38 that is attached to the wall.

Figure 3:
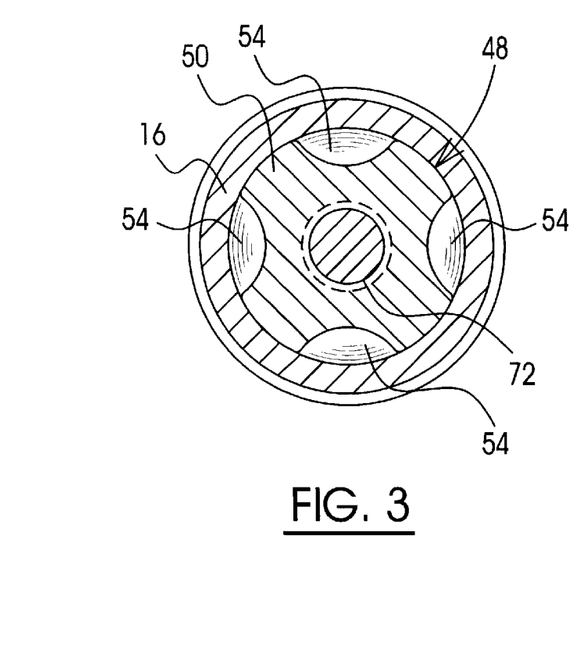
FIG. 3 is a cross-sectional view of the valve body taken along line 3—3 in FIG. 1a, showing the axial flow passages thereof.

A valve body 48 generally is a cylindrical stem having a front portion 50 and rear portion 52. The front portion 50 has an external diameter fitting into the internal diameter of the rear portion 16 of the cylindrical body 12 and permitting the valve body 48 to slide therealong. Axial flow passages 54 are provided, which allow the gas to flow through. The axial flow passages 54, as illustrated in FIG. 3, are four axially extending grooves on the front portion 50 of the valve body and circumferentially spaced apart from one another by the radially extending portions which guide the axial movement of the valve body 48. The rear portion 52 of the valve body is provided with an O-ring seal 56 which is restrained between two annular ridges 58 and 60.

An annular recess 62 is defined between the front portion 50 and the rear portion 52 to provide an annular passage for the gas entering the axial flow passages 54.

Figure 1B:
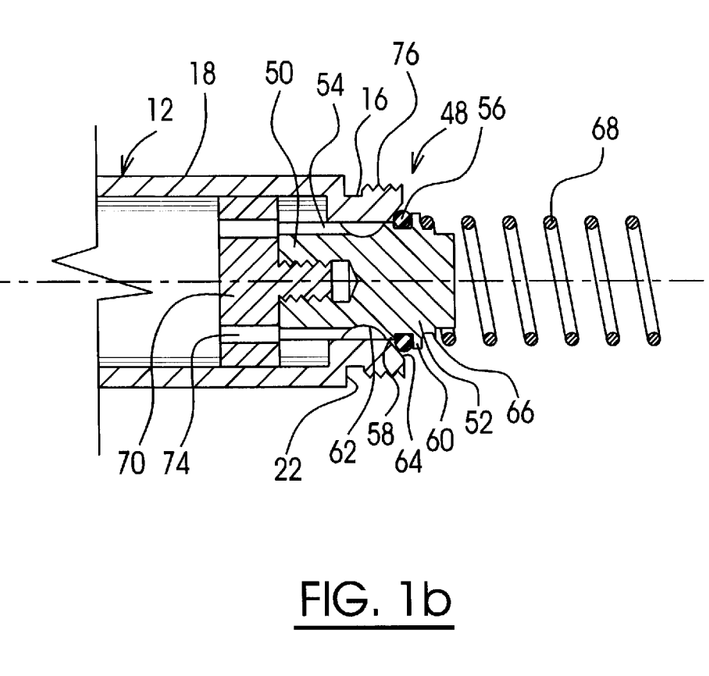
FIG. 1b is a partial longitudinal cross-sectional view of the embodiment in FIG. 1a, in which the secondary valve is in a closed position.

An annular seating surface 64 is defined on the rear end of the rear portion 16 of the cylindrical body 12 to which the O-ring seal ring 56 will abut to close the passage for the gas entering the axial flow passages 54, when the valve body 48 is axially moved towards the left to its final position, shown in FIG. 1b.

The annular ridge 58 has an outer diameter smaller than that of the annular ridge 60 to avoid interference with the sealing when the Q-ring seal 56 abuts the seating surface 64.

Another annular ridge 66 is provided behind the annular ridge 60 to retain a front end of a spiral spring 68. A rear end of the spiral spring 68 will reach an inner end of the cylindrical housing 222 of a wall outlet 220 (FIG. 5a) and force the valve body 48 to move towards the left to close the secondary valve when the secondary valve unit 10 is inserted into the cylindrical housing 222.

A valve retainer 70 is provided to prevent the valve body 48 from being separated from the cylindrical body 12. The valve retainer 70 has an external diameter slidably fitting into the inner diameter of the middle portion 18 of the cylindrical body 12, and a threaded rear end detachably engages a threaded bore 72 (shown in FIG. 3) which axially and inwardly extends from the front end of the valve body 48. A plurality of bores 74 extend axially through the valve retainer 70, and are circumferentially spaced apart from one another, acting as to diffuse the gas flow.

Figure 4:
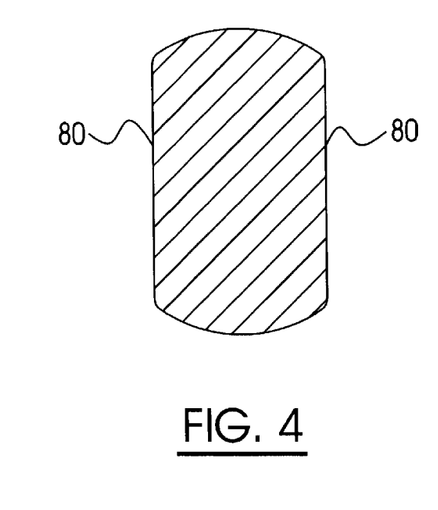
FIG. 4 is a cross-sectional view of the rear end of the valve body taken along line 4—4 in FIG. 1a, showing the opposed flat surfaces thereof for being gripped by a wrench during assembly of the secondary valve unit.

Threads 76 are provided on the exterior of the rear portion 16 of the cylindrical body 12 for threadedly engaging the corresponding threads provided within the cylindrical housing of the wall outlet to secure the secondary valve unit 10 to the wall outlet. Four axial recesses 78 are provided on the annular ridge 34 for receiving a tip of a special tool 300 shown in FIG. 8a to rotate the cylindrical body 12 to engage or disengage the secondary valve unit to or from the existing wall outlet body. The rear end of the rear portion 52 of the valve body is provided with two opposed flat surfaces 80, as shown in FIG. 4 to be gripped by a wrench during assembly or disassembly of the secondary valve unit 10, which will be explained hereinafter with reference to FIG. 8a.

The inner diameter of the middle portion 18 of the cylindrical body 12 and the inner diameter of the annular seal 26 are determined in accordance with the external diameter of the tubing 82 of the AMICO front/finish assembly 84. The inner diameter of the annular seal 26 is slightly smaller than the outer diameter of the tubing 82 so that the annular seal 26 firmly seals the exterior of the tubing 82 when the tubing 82 is inserted into the cylindrical body 12.

Figure 2:
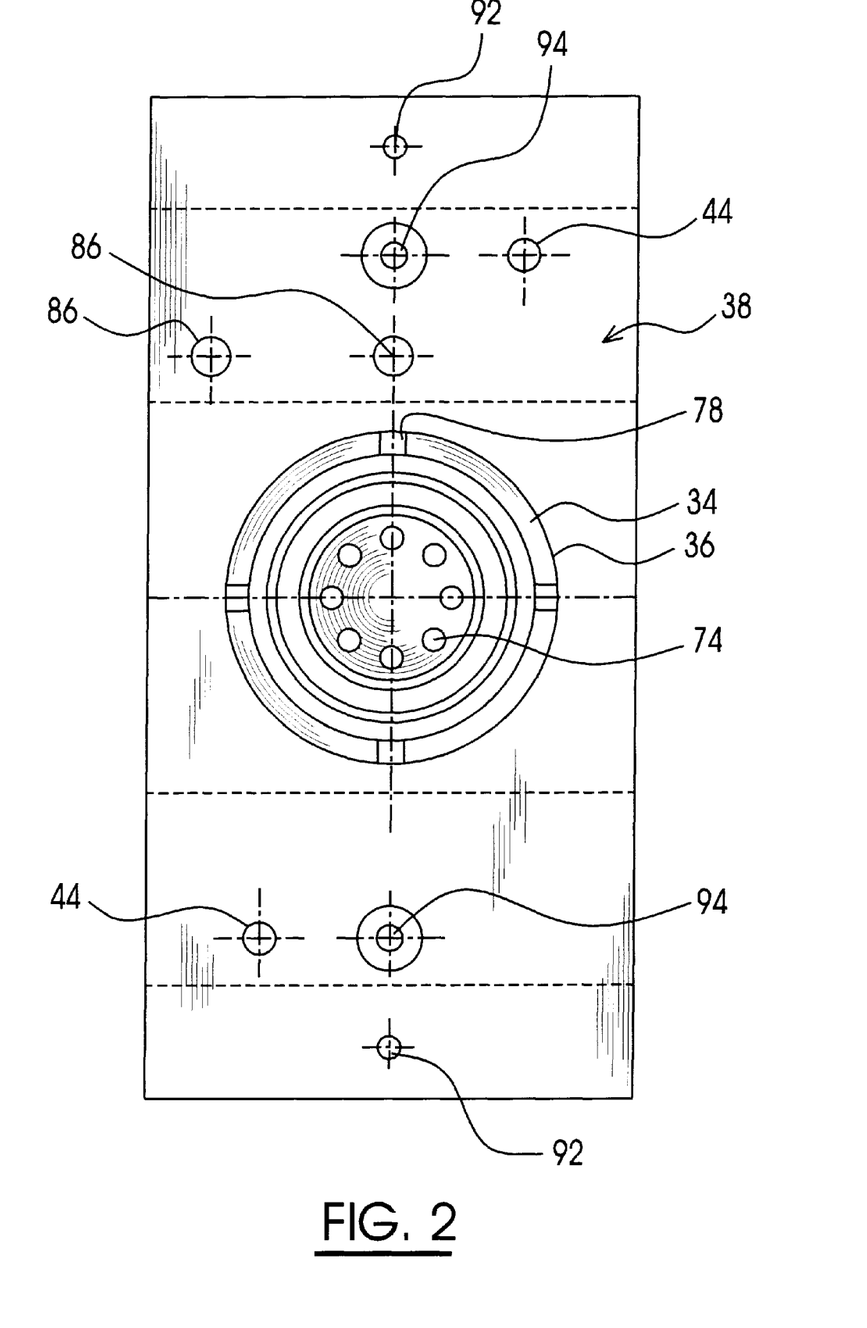
FIG. 2 is a front elevational view of the embodiment in FIG. 1a showing the indexing plate.

Indexing holes 86 are provided in the indexing plate 38 and the bracket 40. The number, size and position of the indexing holes 86 are determined by the configuration of the indexing pins on the AMICO front/finish assembly respective of the type of gases and enabled to receive the corresponding indexing pins 88 of the front/finish assembly 84 which is enabled to be connected only for the gas of the type which is supplied from the wall outlet through the secondary valve unit 10. The front/finish assembly is not part of the invention and is known as AMICO products.

In operation, the valve body 48 with the valve retainer 70, is forced to the extreme left position, as shown in FIG. 1b, and the O-ring seal 56 abuts the seating surface 64 to close the axial passage 24 of the cylindrical body 12 when the secondary valve unit 10 is connected to the wall outlet and the spiral spring 68 is compressed by the inner end of the cylindrical housing of the wall outlet. This is to permit the front/finish assembly to be easily removed from the wall unit without any gas leakage.

In a normal condition, however, the front/finish assembly is installed to the wall outlet and the tubing 82 is inserted into the cylindrical body 12 to press the valve retainer 70 and the valve body 48 back to the extreme right position, shown in FIG. 1a, or intermediate positions therebetween so that the secondary valve remains open. The primary valve (not shown) in the tubing 82 of the front unit 84 normally is closed and, therefore, the gas is not able to escape even though the secondary valve normally remains open. When an adapter of gas equipment, not shown, is connected to the end 90, a plunger of the adapter will open the primary valve in the tubing 82 to permit the gases to flow through the secondary and the primary valves into the equipment.

Mounting bores 92 are provided in the indexing plate 38 to receive two rivetnuts which are rivets having central bores with inner threads. The rivetnuts received in the mounting bores 92 permanently fasten the indexing plate to the wall, which meets the requirement of the standard to reduce the risk that the unit 10 is accidentally removed from the wall outlet. Mounting bores 94 are provided in both of the indexing plate 38 and the bracket 40 for receiving two rivetnuts, the inner threads of which are adapted to engage two threaded bolts to secure the front/finish assembly to the indexing plate 38.

Figure 5A:
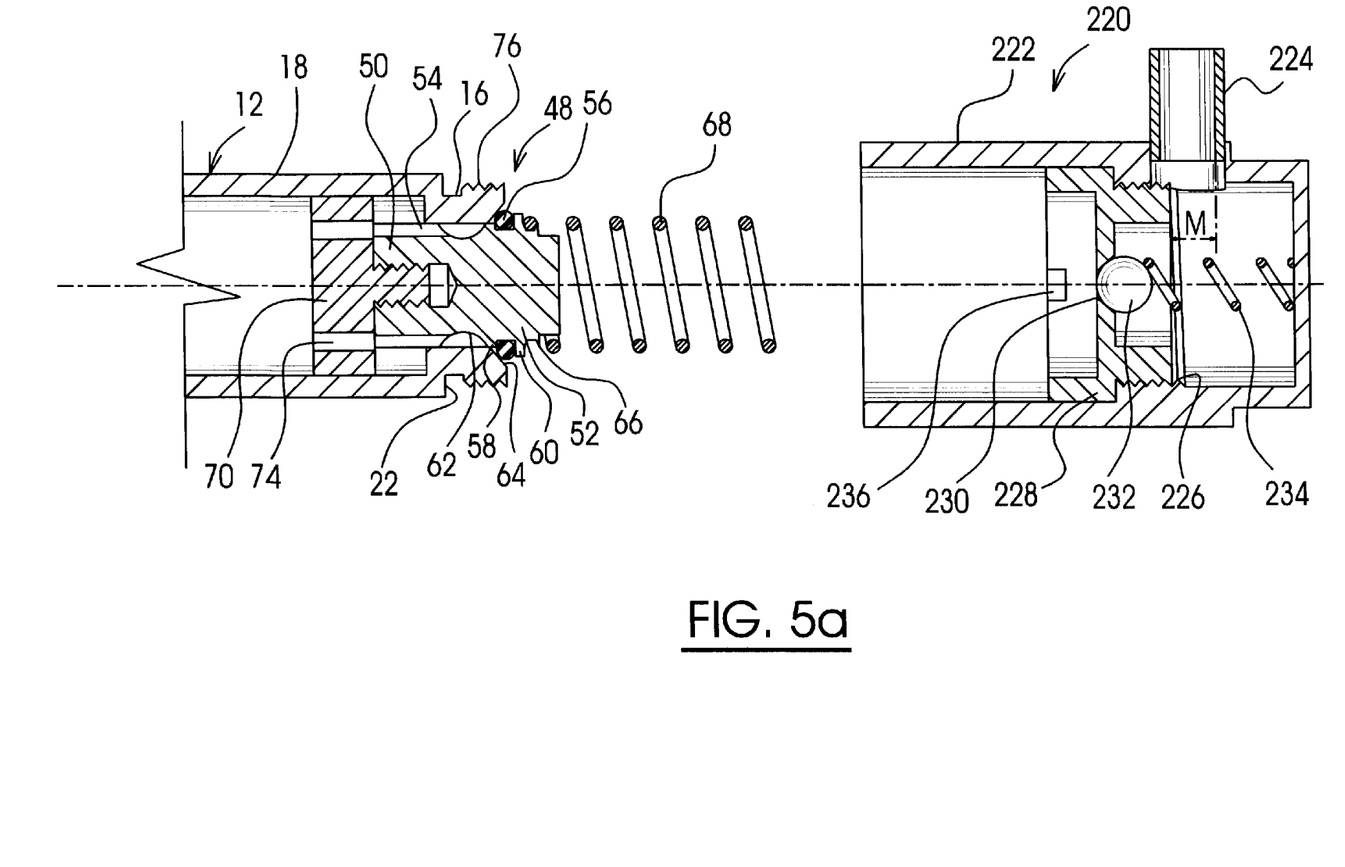
FIG. 5a is a partial cross-sectional view of the embodiment in FIG. 1a to be connected to an existing wall outlet of one type.
Figure 5B:
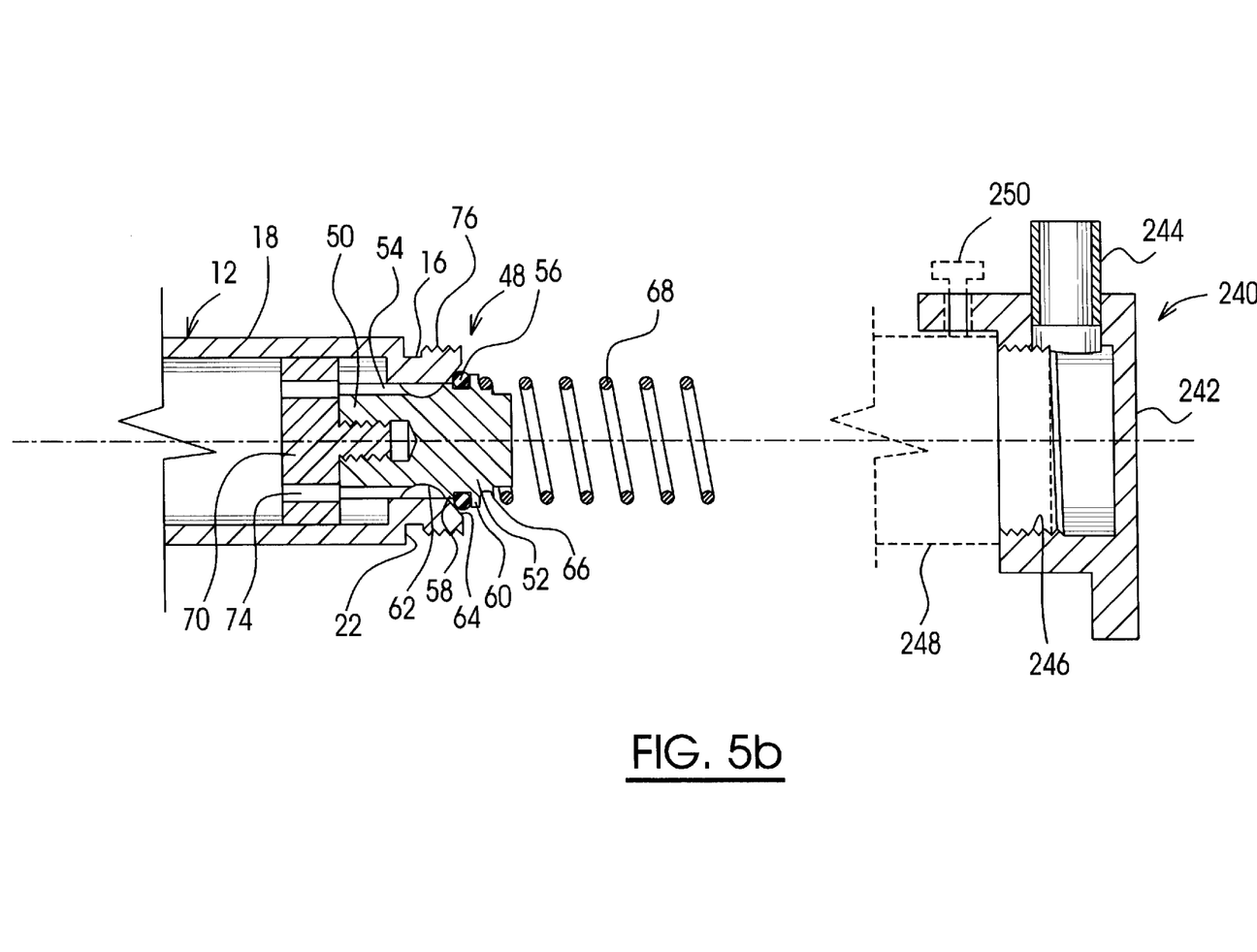
FIG. 5b is a partial cross-sectional view of the embodiment in FIG. 1a to be connected to an existing wall outlet of another type.

The secondary valve unit 10 is especially used for two types of existing OHMEDA wall outlets as shown in FIGS. 5a and 5b. One type of wall outlet 220, shown in FIG. 5a, includes a cylindrical housing 222 welded to a pipe 224 which is in fluid communication with a medical gas source. The cylindrical housing 222 has inner threads 226 which engages a retainer 228. The retainer 228 includes a central bore 230 defining a valve seat to receive a ball valve 232. The ball valve 232 is biased by a spring 234 to the closed position as shown.

A pair of diametrically opposed recesses 236 are provided at the front end of the retainer 228 for engaging a tool tip to loosen or tighten the retainer 228. During a renovation of the medical gas system, the retainer 228, valve ball 232 and the spring 234 are removed from the cylindrical housing 222, and the pre-assembled secondary unit 10 (only partially shown) is inserted into the cylindrical housing 222. The screws in bores 44 (see FIG. 2) in the indexing plate 38 are not tightened in the pre-assembled unit and the cylindrical body 12 is permitted to rotate relative to the indexing plate 38 so that the threads 76 of the cylindrical body 13 is able to engage the threads 226 of the cylindrical housing 222. An O-ring seal (not shown) may be provided to seal the connection. After the threaded connection is tightened, the screws in bores 44 are tightened to prevent the cylindrical body 12 from rotation. There is no need for applying the Loctite 271 to the threaded connection as is required with other manufacturers kits and the fire risk is eliminated.

In order to ensure a large gas flow over the secondary valve unit, a minimum gas flow cross-sectional area in the secondary valve unit 10 should be close to, preferably not smaller than, a minimum (limiting) gas flow area in the gas system at upstream with respect to the unit 10. The minimum (limiting) gas flow area in the existing system using OHMEDA wall outlets, is the area indicated as M, equal to the cross-section of the inner passage of the pipe 224 minus the area overlapped by the threaded rear end of the retainer 228. The area M remains about the same when the secondary unit 10 is connected. Therefore, the gas flow area defined respectively by the axial flow passages 54 and bores 74, especially defined by the interface of the passages 54 and bores 74, is preferably greater than the area M.

The second type of OHMEDA wall outlet 240 shown in FIG. 5b includes a body 242 welded to a pipe 244 which is in fluid communication with a medical gas source. Threads 246 are provided to connect an existing unit 248 which includes a secondary valve (not shown). The threaded connection is locked by the screw 250. After the screw 250 is loosened or removed, the unit 248 is removed. Following the procedure described with reference to FIG. 5a, the secondary valve unit 10 which is partially shown in FIG. 5b is installed to the body 242.

Figure 6:
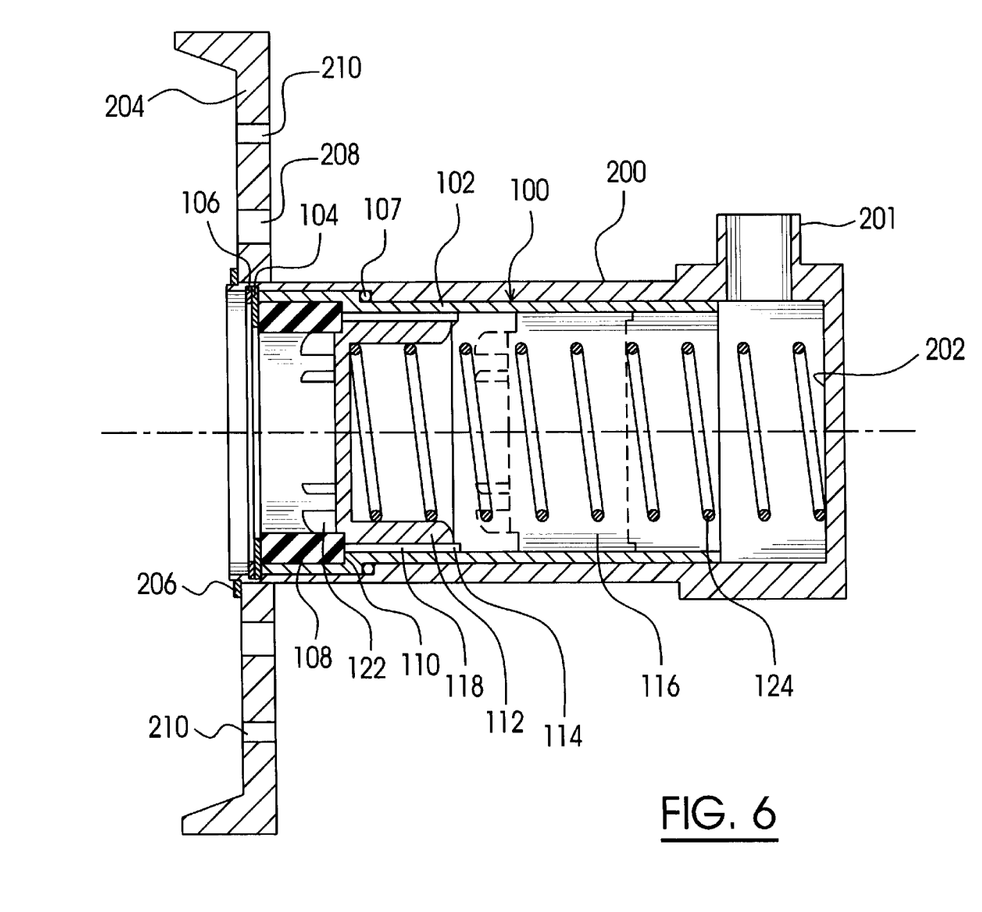
FIG. 6 is a longitudinal cross-sectional view of another preferred embodiment of the invention, which is installed within a housing of an existing wall outlet of a third type.

In FIG. 6, there is another embodiment in accordance with the present invention, especially used for a third type of OHMEDA wall outlets. The secondary valve assembly 100 includes a cylindrical body 102, which is restrained within a cylindrical body 200 of an existing wall outlet by a washer 104 and an annular spring retainer 106 after all existing inner parts (not shown) within the cylindrical body 200 are removed. The cylindrical body 200 is welded to a pipe 201 connected with a medical gas source and is a type different from the cylindrical body 222 and the body 242 of the existing wall outlets 220 and 240 described above. Therefore, the cylindrical body 102 is configured differently from the cylindrical body 12 in the secondary valve unit 10 and, particularly, the exterior and the two ends thereof have to fit into the interior of the cylindrical housing 200.

An O-ring seal 107 is provided between an annular shoulder on the exterior of the cylindrical body 102 and an annular step on the interior of the cylindrical body 200 to further restrain and seal the cylindrical body 102 to prevent gas leakage. An annular resilient seal 108 is snugly received in the cylindrical body 102 at the front end and axially restrained between the washer 104 and an annular step 110 on the interior of the cylindrical body 102.

Figure 7:
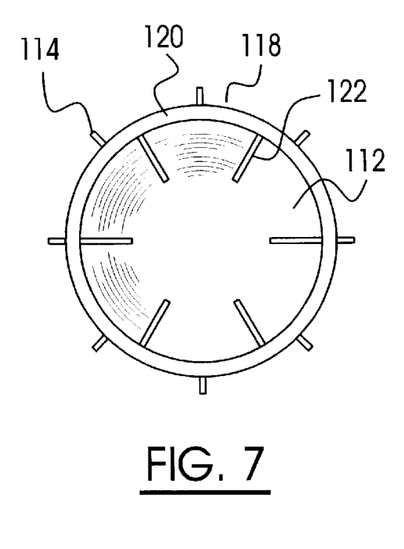
FIG. 7 appears on the sheet of FIGS. 3 and 4 and is a front view of the valve body in FIG. 6.

The annular seal 108 serves as both a seal which sealingly receives the tubing of the front/finish assembly (not shown) to be inserted therethrough and a valve seat which receives a valve body 112 to be seated thereon. The valve body 112 is a plastic cylindrical sleeve with a closed front end. A plurality of axially extending ridges 14 are provided on the external periphery of the valve body 112, and circumferentially spaced apart from one another, as shown in FIG. 7. The valve body 112 is slidable in an axial passage 116 of the cylindrical body 102, being guided by the axially extending ridges 114.

Adjacent ridges 114 define gas flow passages 118 extending axially therebetween. The closed front end of the valve body 112 includes an annular shoulder 120 to snugly fit into the rear end of the annular seal 108 to close the axial passage 116 of the cylindrical body 102. A plurality of projecting members 122 radially extending on the closed front end of the valve body 112, are adapted to guide the valve body 112 to be properly seated on the rear end of the annular seal 102.

A spiral spring 124 is placed between the valve body 112 and an inner end 202 of the cylindrical body 200 to maintain the valve body 112 to be seated at the rear end of the annular seal 108 and close the axial passage 116. When the tubing of the front/finish assembly is inserted into the axial passage 116 of the cylindrical body 102, the tubing moves the valve body 112 rearwards against the spring force to an open position, shown in broken lines, in which the gas flow is able to pass the valve body 112 through the gas flow passages 118 between the ridges 114.

The gas flow area defined by the gas flow passages 118 is close to, or preferably not smaller than, the gas flow area defined by the pipe 101 to ensure a great gas flow.

The cylindrical body 200 is already attached to a wall plate 204 in the existing wall outlet using an annular retainer 206. Existing indexing bores (not shown) in the wall plate 204 is not adapted for use with the AMICO front unit and, therefore, new indexing bores 208 are drilled in the wall plate 204 and adapted to receive the corresponding indexing pins of the AMICO front unit. The indexing bores 208 can be accurately drilled using a set of templates, also provided. Mounting bores 210 are already provided in the existing wall plate.

It is convenient to provide a kit including all parts for the different secondary valve units adapted for the respective manufacturers of wall outlets during a renovation project. The kit may further include a tool especially for use in assembly and disassembly of the secondary valve units according to the invention.

Figure 8A:
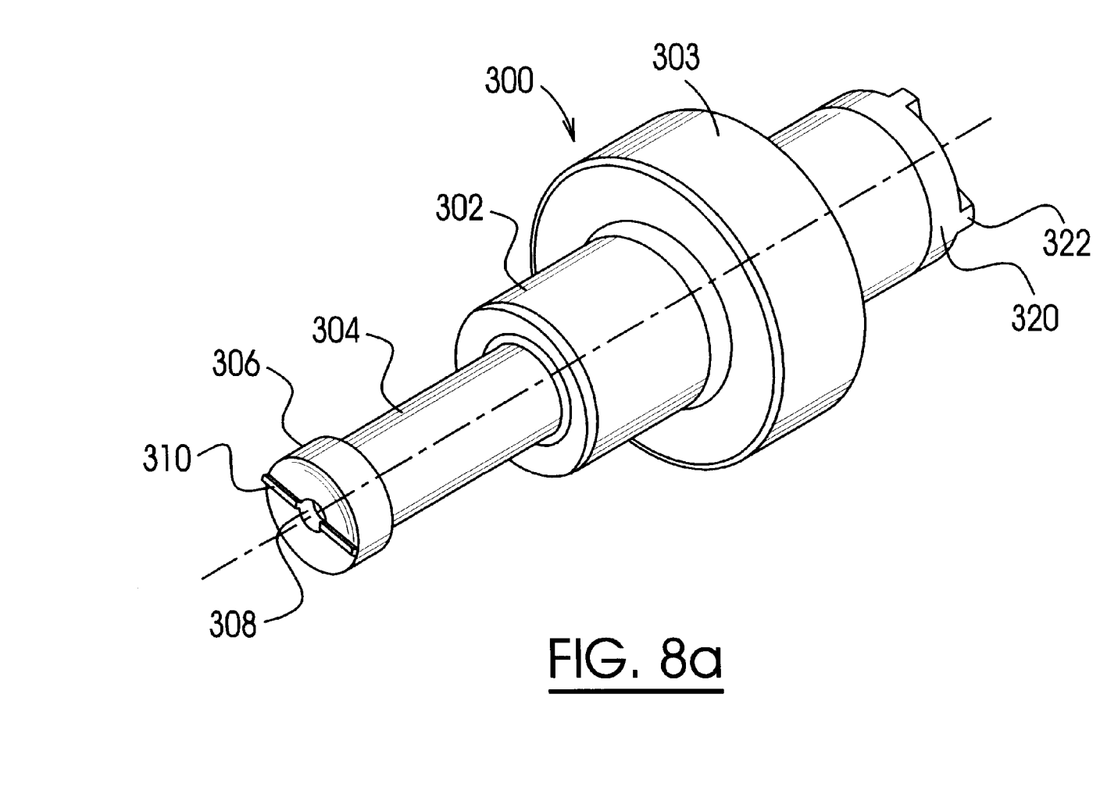
FIG. 8a is a perspective view of a tool used especially for assembly or disassembly of the embodiment in FIG. 1.

In FIG. 8a, a tool 300, designed especially for such a purpose, includes a cylindrical body 302 which has an external diameter about equal to that of the front portion 14 of the cylindrical body 12 in the embodiment shown in FIG. 1a. A middle portion 303 of the cylindrical body 302 has a greater diameter for being gripped by a user's hand to apply torque to the tool 300. A stem 304 axially extends from one end of the cylindrical body 302 and has a length greater than a distance from the extremity of the front end of the cylindrical body 12 to the retainer 70 that is in the right most position, as shown in FIG. 1a. A tip 306 for wall outlets is secured to the end of the stem 304 using a screw (not shown) received in a central bore 308. A ridge 310 extends radially across the outer end of the tip 306 for engaging the diametrically opposed recesses 236 of the retainer 228 (see FIG. 5a) for applying a torque to loosen the retainer.

Figure 8B:
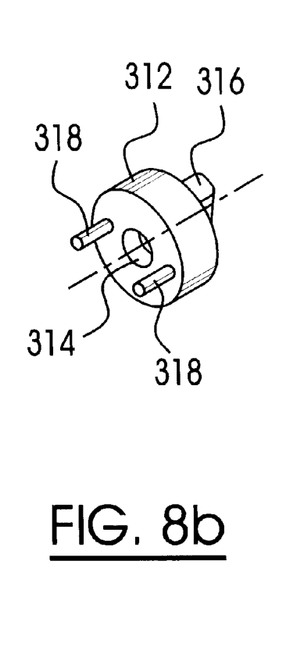

Another tip 312 is provided for interchanging with the tip 306. The tip 312, shown in FIG. 8b, similar to tip 306, is cylindrical and has a central bore 314 axially extending therethrough for receiving a screw to secure the tip to the stem 304. A projecting member 316 which is also included in tip 306 but is not shown, is provided on the inner end of the tip 312, extending radially to cooperate with a female member (not shown) inside the stem 304 for transmitting a torque applied to the tool. Two pins 318 are provided at the outer end of the tip 312, which are adapted to fit into a pair of diametrically opposed bores 74 in the retainer 70 in FIGS. 1a and 1b. The outer diameter of the tip 312 is slightly smaller than the inner diameter of the annular seal 26 to enable the tip to be easily inserted into the passage 42 of the cylindrical body 12.

Figure 8C:
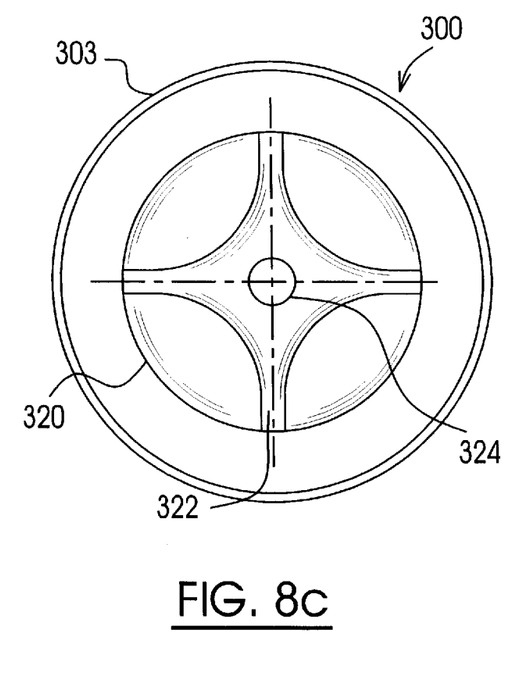

At the other end of the cylindrical body 302, is provided a tip 320. Four male members 322 are provided at the outer end of the tip 320 and a central bore 324 is included for receiving a fastening screw (not shown), which is more clearly shown in FIG. 8c. The four male members 322 are adapted to fit into the recess 78 of the annular ridge 34 of the cylindrical body 12 in FIG. 1a to apply a torque to the cylindrical body 12 to rotate the same for threadedly engaging or disengaging from a cylindrical body of the wall outlet. Similar to the projecting member 316 on the tip 312, a projecting member (not shown) is provided on the tip 320 for torque transmission.

When the retainer 70 and the valve body 48 are to be assembled or disassembled, a wrench (not shown) is to be used to grip the two opposed flat surfaces 80 (see FIG. 4) at the rear end of the valve body 48, and the tip 312 attached to the tool 300 is inserted into the axial passage 24 until the two pins 318 engage the corresponding bores 74 in the retainer 70. Thus, a torque is enabled to be applied to the retainer to rotate the same for threadedly engaging or disengaging from the valve body 48.

The embodiments described above may be used for oxygen, vacuum, air and any other type of the medical gases, and are examples only for illustrating the principles of the invention. Modifications and improvements to the above-described embodiments of the invention, may become apparent to those skilled in the art. The foregoing description is intended to be exemplary rather than limiting. The scope of the invention is therefore limited solely by the scope of the appended claims.

The embodiments of the invention in which an exclusive property of privilege is claimed are defined as follows:

1. A kit for a connector unit for gases which is used to connect a wall outlet of a gas system to a front unit having a primary valve tube, comprising:
   a cylindrical body adapted to be detachably connected with the wall outlet, and defining an axial passage extending therethrough;
   a secondary valve adapted to be secured to the cylindrical body, the secondary valve being biased to close the axial passage when the cylindrical body is connected to the wall outlet, and being always open when the front unit is mounted to the wall and the primary valve tube is inserted into the passage of the body;
   a seal adapted to be contained within the cylindrical body for sealing an exterior of the primary valve tube when the front unit is mounted to the wall; and
   means for securing the connector unit to the wall outlet when the cylindrical body is connected to the wall outlet.

2. A kit as claimed in claim 1 comprising:
   a plate having an aperture, adapted to be attached to a front end of the cylindrical body, with the aperture aligned with the passage of the cylindrical body, for securing the connector unit to the wall while permitting the primary valve tube of the front unit to be inserted through the aperture into the passage of the cylindrical body; and
   indexing means provided with the plate, adapted for co-operation with corresponding indexing means of the front unit to ensure that a front unit specified only for use with a gas of the type supplied from the wall outlet is enabled to be connected to the connector unit.

3. A kit as claimed in claim 2 wherein the secondary valve comprises a valve body and a valve retainer for retaining movement of the valve body within a predetermined axial range.

4. A kit as claimed in claim 3 wherein the cylindrical body includes a valve seat for receiving the valve body seated thereon to close the axial passage of the cylindrical body.

5. A kit as claimed in claim 4 wherein the valve body comprises guiding means for slidably centring the valve body in the axial passage.

6. A kit as claimed in claim 5 wherein the valve body comprises a plurality of axial gas flow passages circumferentially spaced apart from one another to permit gas flowing past the valve body.

7. A kit as claimed in claim 6 wherein the valve retainer comprises a plurality of axially extending bores for diffusing the gas flow in the axial passage of the cylindrical body.

8. A kit as claimed in claim 7 wherein a total gas flow cross-sectional area defined by the axial flow passages of the valve body is at least as large as a smallest flow orifice located upstream in the gas system so as to reduce a pressure drop through the connector unit during delivery of the gas.

9. A kit as claimed in claim 8 wherein a total gas flow cross-sectional area defined by the axially extending bores of the valve retainer is at least as large as the upstream smallest flow orifice.

10. A kit as claimed in claim 7 comprising a spring adapted to force the valve body to abut the valve seat when the cylindrical body is connected to the wall outlet.

11. A kit as claimed in claim 1 comprising an additional adapter to interconnect the front unit and a wall outlet of a different type, the adapter including at least a cylindrical sleeve body having an exterior fitting into an interior of the wall outlet of the different type and an interior for operatively receiving an exterior of the valve tube of the front unit.

12. A connector unit for gases used to connect a wall outlet of a gas system to a front unit having a primary valve tube comprising:
    a cylindrical body adapted to be detachably connected to the wall outlet, and defining an axial passage extending therethrough;
    a secondary valve secured to the cylindrical body, the secondary valve being biased to close the axial passage when the cylindrical body is connected to the wall outlet, and being always open when the front unit is mounted to the wall and the primary valve tube is inserted into the passage of the body;
    a seal contained within the cylindrical body for sealing an exterior of the primary valve tube of the front unit when the front unit is mounted to the wall;
    a plate having an aperture adapted to be secured to a front end of the cylindrical body for attachment of the assembly to the wall while permitting the primary valve tube of the front unit cylindrically to be inserted through the aperture into the passage of the body;
    and indexing means provided with the plate, adapted for co-operation with corresponding indexing means of the front unit to ensure that a front unit specified only for use with a gas of the type supplied from the wall outlet is enabled to be connected to the connector unit.

13. A connector unit as claimed in claim 12 wherein the cylindrical body includes a threaded connector at a rear end adapted to engage the wall outlet.

14. A connector unit as claimed in claim 13 wherein the cylindrical body includes engaging members at the front end thereof adapted for engaging a tool which applies a torque on the cylindrical body to rotate the same for installation.

15. A connector unit as claimed in claim 13 comprising a holding bracket and a resilient gasket which firmly secure the cylindrical body to the plate to prevent the cylindrical body from rotation relative to the plate.

16. A connector unit as claimed in claim 12 wherein the indexing means is defined by one or more indexing bores in the plate, which are sized and located in accordance to the configuration of the indexing pins of the front unit.

17. A connector unit as claimed in claim 12 wherein the rear end of the cylindrical body defines a valve seat and the secondary valve includes a valve body with a plurality of gas flow passages, the valve body being enabled to abut the valve seat and close the gas flow passages.

18. A connector unit as claimed in claim 17 wherein the secondary valve comprises a valve retainer for being detachably secured to the valve body to prevent the valve body from separation from the cylindrical body.

19. A connector unit as claimed in claim 18 wherein the valve retainer comprises a plurality of axially extending bores which are positioned so that each of the bores is in full fluid communication with an interior of the primary valve tube of the front unit for freely delivering the gas flow into the primary valve tube of the front unit which abuts the valve retainer when the front unit is connected to the connector unit and the primary valve tube is open for the gas flow.

20. A connector unit as claimed in claim 19 wherein a total gas flow cross-sectional area defined by an interface of flow passages in valve body and bores in valve retainer is not smaller than a gas flow cross-sectional area defined in an interface between the wall outlet and a pipe which connects the wall outlet with a gas source.

* * * * *